United States Patent [19]

Goode

[11] Patent Number: 4,630,492

[45] Date of Patent: Dec. 23, 1986

[54] AUTOMATIC STAPLE FIBER SAMPLER

[75] Inventor: Sidney H. Goode, Spartanburg, S.C.

[73] Assignee: American Hoechst Corporation, Somerville, N.J.

[21] Appl. No.: 803,362

[22] Filed: Dec. 2, 1985

[51] Int. Cl.⁴ .............................................. G01N 1/02
[52] U.S. Cl. ................................................... 73/863.82
[58] Field of Search .......... 73/863.41, 863.51, 863.54, 73/863.81, 863.85, 864, 864.31, 864.32, 864.71, 864.83, 863.82

[56] References Cited

U.S. PATENT DOCUMENTS

| | | | |
|---|---|---|---|
| 1,521,545 | 12/1924 | Kistler | 73/863.41 |
| 3,315,530 | 4/1967 | Woodley, Jr. | 73/864 |
| 3,554,038 | 1/1971 | Sweeney et al. | 73/863.83 |
| 3,595,087 | 7/1971 | Starks | 73/863.54 |
| 3,659,461 | 5/1972 | Thompson | 73/863.54 |
| 3,746,217 | 9/1973 | Hanset et al. | 73/863.73 |
| 3,841,159 | 10/1974 | Wilder et al. | 73/863.41 |
| 3,949,614 | 4/1976 | Abonnenc | 73/863.83 |
| 4,024,765 | 5/1977 | Abonnenc | 73/863.83 |
| 4,027,537 | 6/1977 | Van Doorn et al. | 73/865.24 |
| 4,170,900 | 10/1979 | Ozawa | 73/863.02 |
| 4,433,587 | 2/1984 | Risdal | 73/863.54 |

OTHER PUBLICATIONS

J. Sherrill, "Sampler Assembly," Drawing No. D-3600 (Jul. 24, 1981).

Primary Examiner—Michael J. Tokar
Assistant Examiner—Robert R. Raevis
Attorney, Agent, or Firm—James C. Lydon

[57] ABSTRACT

An apparatus and method for sampling falling staple fiber is disclosed. The apparatus employs air pressure within the sampler housing which is substantially equivalent to the air pressure within the fiber chute to be sampled, in combination with a rod-like sample probe having a smooth, convex fiber-sampling section at one rounded end and, opposite thereto, a mounting means engagement end, with at least one protrusion mounted on said fiber-sampling section at or near said rounded end.

19 Claims, 8 Drawing Figures

AUTOMATIC STAPLE FIBER SAMPLER

BACKGROUND OF THE INVENTION

The present invention relates to an improved apparatus and method for accurately sampling staple fibers. More particularly, the present invention relates to a static-air-pressurized automatic sampler having a smooth, convex fiber sample collection surface.

There are several generic manufacturing processes which may be employed in the production of staple synthetic fibers, including "melt spinning", "wet spinning", and "dry spinning." These three manufacturing processes differ from one another by the extrusion method they employ. As disclosed in the published literature, many specific variants of each of the three generic processes have been developed. However, all of these processes have in common the assembly of fiber bundles comprising many thousands of filaments, subsequently followed by cutting these into relatively short or staple fiber. Clumps of the cut staple fiber, of varying size and density, fall out of the cutting apparatus, either directly into the baler or into a transfer system which conveys them to a baler.

A typical process for the manufacture of polyester staple fibers may be briefly described as follows. Polyester resin, typically in chip form, is melted in an extruder and is pumped via a plurality of metering pumps through a filter packing and then through a multiple-hole spinnerette, which forms the molten polyester into a plurality of filament-like forms. The extruded filament-like forms are immediately cooled below the glass transition temperature of the polyester, thereby forming the actual filaments. A fiber finish composition is applied to the cooled polyester filaments. The filaments from all spinnerettes of the spinning machine are plied to form a spin cable, which is typically collected by deposition into a large can. The spin cables from a plurality of cans are subsequently fed from a creel to a stretch line. The assembly of spin cables on the stretch line (typically termed a "tow" or "tow band") is recoated with the fiber finish, and stretched to orient the filaments. In order to provide cohesion between the fibers necessary for subsequent textile processing, the fiber tow is crimped in a stuffer box, which produces a relatively wide band of crimped fiber called a crimper tow. The crimper tow is heat set, cut into staple fiber and baled. Alternatively, in order to produce fiber possessing a higher modulus, the fiber tow may be crimped after being heat-set, then cut into staple fiber and baled.

In the manufacture of staple fibers it is important to monitor and control various chemical and physical characteristics of the fibers, such as denier, tenacity, elongation at break, modulus, shrinkage in hot air or hot water, finish content, quantity of fused or undrawn fibers present, the length of the fibers, and their "openness" (the density and cohesiveness of the staple fiber mass). It is well known that these and other chemical and physical characteristics of staple fibers are strongly predictive of the performance of these fibers in the subsequent processes by which these fibers are converted into finished products and strongly influence the characteristics of the finished products. The chemical and physical characteristics of staple fibers must be controlled within limits appropriate to the intended application(s) if the fibers are to be suitable for the intended application(s). An accurate knowledge of the chemical and physical characteristics of staple fibers is necessary for proper control of the staple fiber manufacturing process, and for accurate grading of the product.

The many manufacturing circumstances which can lead to unintended and inappropriate chemical and physical staple fiber characteristics may be classified into two groups: "continuous circumstances" which operate continuously to consistently produce unintended characteristics, and "intermittent circumstances" which operate intermittently to produce isolated "pockets" of fibers with unintended characteristics. Testing of any staple fiber sample taken will normally reveal defects which are being produced continuously in the manufacturing process. However, other defects occurring only intermittently are not likely to be reliably detected unless the sample tested is statistically representative of the staple fiber product increment represented.

Manual sampling of staple fibers as they fall from the yarn cutting apparatus to a baler is still a commercial practice. Normal procedure has been to open a sampling port and manually grab a handful of falling staple fiber, which is then analyzed for length and "openness". The sampling frequency is typically one grab per fiber bale (normally either 500 or 750 pounds). This method is both expensive and ineffective in providing statistically representative samples.

Staple fibers have also been manually sampled after they have been baled. Typically, the baler operator hand-pulls three samples from the face of the bale—one handful of fiber in the middle, one handful from the upper right hand corner and one handful from the lower left hand corner. This method is also expensive and statistically unrepresentative. The manual pulling of staple fiber from the baled fiber mass often breaks individual fibers, thereby leading to inaccurate fiber length analysis. Furthermore, accurate analysis of the "openness" of the fibers is impossible once they have been compressed into a bale.

Prior artisans have proposed automatic sampling of staple fibers. For example, M. Wilder et al, "Automatic Sampler for Flowing Staple Fiber," U.S. Pat. No. 3,841,159 (Oct. 15, 1974) discloses a sealed yarn sample container connected to a yarn transfer line by a conduit. The container has supported internally a yarn catching means such as a hook which may be thrust through the conduit into the transfer line where it catches a small wad of flowing staple. Then the yarn catching means is returned to the sample container where the fiber sample drops off by gravity into the container. The entire sample container is sealed to withstand the pressure of the transfer line, thereby precluding the removal of sample for analysis while the sampler is operating.

J. Woodley, Jr., "Fiber Sampling Apparatus," U.S. Pat. No. 3,315,530 (Apr. 25, 1967) discloses an automatic fiber sampler located between the yarn cutting apparatus and a fiber packaging system. The fiber sampler comprises a housing adjacent the fiber stream to be sampled, a hollow probe reciprocably mounted in the housing, the hollow probe having one end open and the other terminating in a probe tip of specific design. In operation partial vacuum is applied to the probe tip by aspiration, thereby attracting and holding a sample of fiber from the fiber stream. The probe is then withdrawn from the fiber stream. When the probe is fully retracted pressurized air is sent through the hollow probe, thereby blowing the retained staple fiber sample off the probe tip and through a transfer chute into a sample collection box.

The use of suction, like mechanical grabbing, to collect a sample of staple fiber is undesirable since such sampling may alter some of the physical properties of the sampled fibers, thereby providing a statistically unrepresentative staple fiber sample.

Automatic sampling apparatus for other applications have also been proposed, particularly for granular or powdery material. For example, J. Abonnenc, "Automatic Volumetric Device for Taking Samples of Granular or Powdered Material," U.S. Pat. No. 4,024,765 (May 24, 1977) discloses a horizontal, cylindrical sampling probe having a trapezoidal sample recess for the removal of a fixed volume of material from the sampling zone. The sampling probe is reciprocably inserted into and withdrawn from the sampling zone by pneumatic or hydraulic rams. The sampling probe is rotated about its major axis to discharge the sampled material into a sample hopper. The sampler is sealed to prevent contamination by the sampling area. Similarly, R. Starks, "Sampling Apparatus," U.S. Pat. No. 3,595,087 (July 27, 1971) discloses a hollow, rotable, and reciprocal sampling tube for use with granular materials of differing sizes and configurations Other samplers have been proposed for specific applications, typically involving pressurized lines and apparatus or materials under vacuum. For example, D. Sweeney et al, "Sampling Device for Rotary Cone Vacuum Dryer," U.S. Pat. No. 3,554,038 (Jan. 13, 1971) discloses the use of a helical rotating wire to continuously remove sample from an evacuated rotating dryer without having to stop the dryer or release the vacuum. A. Thompson, "Line Sampling Device," U.S. Pat. No 3,659,461 (May 2, 1972) uses a sealed sampler employing a sampling plunger and poppet valves to sample products flowing in a pressurized line such as partially digested wood chips. N. Risdal, "Sampler for Flowing Pressurized Dry Material," U.S. Pat. No. 4,433,587 (Feb. 28, 1984) discloses, inter alia, an inclined sample tube which is alternately projected upwardly into and withdrawn downwardly from the stream of flowing material. The tube has a sample receiving slot in its upstream side and a discharge port in its bottom side. Employing a series of seals and an obstruction in the sample receiving slot, the apparatus can sample from a pressurized line while maintaining its outlet ports at atmospheric pressure.

Research and development resulting in the present invention was initiated only after a commercial automatic sampler was purchased and demonstrated to be unacceptable. Problems associated with the commercial sampler included an unacceptably slow sampling rate, failure to properly release sampled fibers into the sample fiber chute, and contamination of the sampler by staple fibers when the sampler was not operating.

The present invention remedies these problems and in so doing satisfies a long felt but unsatisfied need in the synthetic fiber manufacturing industry for an automatic fiber sampler which can rapidly and repetitively sample staple fibers falling within a fiber chute at a sampling frequency of up to 50 samples per bale.

SUMMARY OF THE INVENTION

In one aspect, the present invention is an apparatus for sampling staple fibers which are falling within a fiber chute comprising:
(i) a sampler housing;
(ii) means for attachment of said sampler housing to a sample port on a fiber chute;
(iii) means for maintaining the air pressure within said sampler housing substantially equivalent to the air pressure within said fiber chute;
(iv) a sample discharge chute attached to said sampler housing;
(v) a rod-like sample probe mounted within said sampler housing having a smooth, convex fiber-sampling section at one rounded end and, opposite thereto, a mounting means engagement end, said fiber-sampling section having at least one protrusion mounted at or near said rounded end;
(vi) means for retractably inserting said rod-like sample probe from within said sampler housing into said fiber chute perpendicularly to the direction of fiber travel;
(vii) means for rotating said rod-like sample probe more than 90 degrees about its major axis from a first, fiber-sampling position to a second, fiber-discharging position;
(viii) means for controlling the movements of said rod-like sample probe by the retractable insertion means and the rotation means.

In another aspect, the present invention relates to a process for sampling fibers which are falling within a fiber chute comprising
maintaining the air pressure within a sampler housing which is attached to a sample port on a fiber chute substantially equivalent to the air pressure within a fiber chute;
inserting a rod-like sample probe mounted within said sampler housing through said sample port into said fiber chute;
collecting a sample of fibers falling within said fiber chute on said rod-like sample probe;
retracting said rod-like sample probe, bearing said fiber sample, through said sample port and into said sampler housing;
rotating said rod-like sample probe more than 90 degrees about its major axis, thereby discharging said fiber sample into a sample discharge chute mounted onto the bottom of said sampler housing;
with the proviso that said rod-like sample probe has a smooth, convex fiber-sampling section at one rounded end and, opposite thereto, a mounting means engagement end, said fiber-sampling section having at least one protrusion mounted at or near said rounded end.

DETAILED DESCRIPTION OF THE INVENTION

Figure 1:
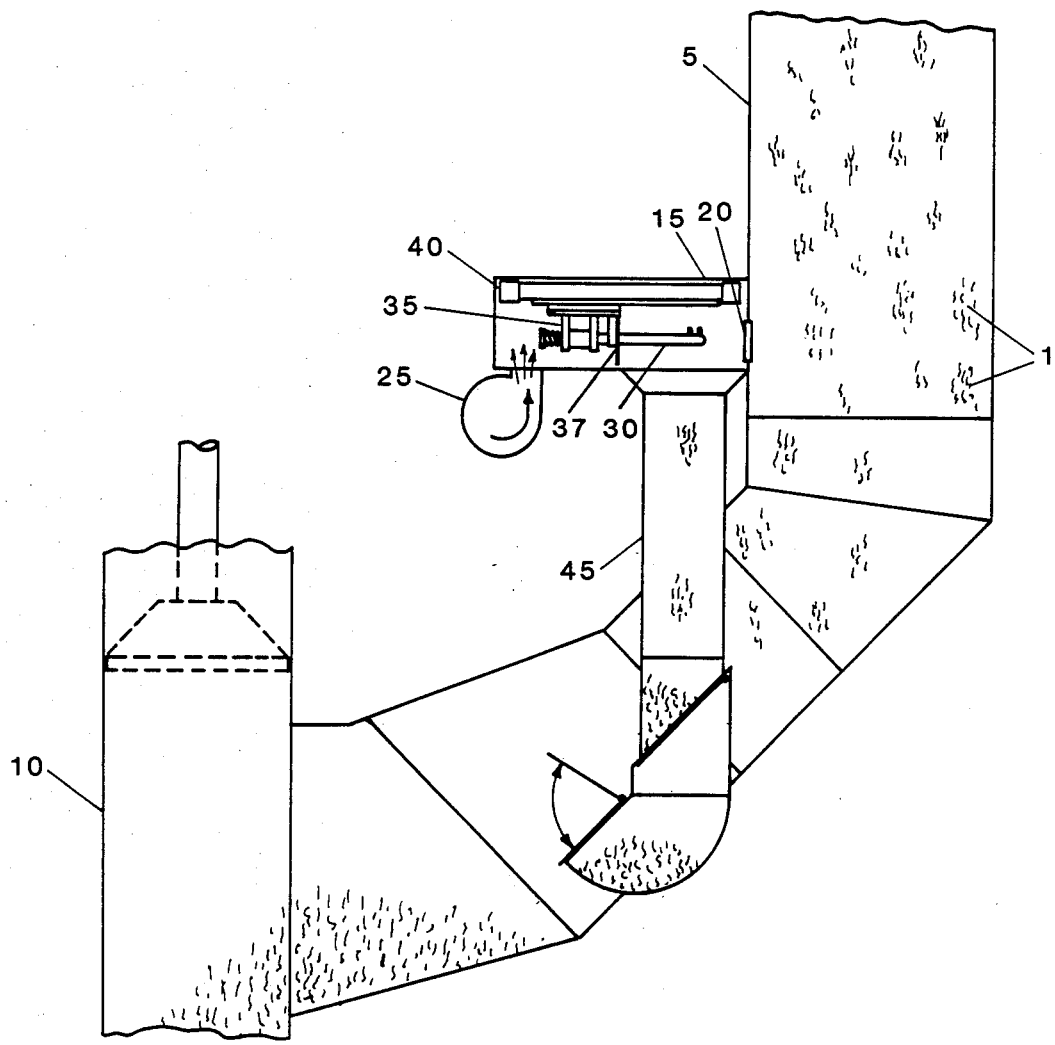
FIG. 1 is a cutaway illustrating the location of the fiber sampler of the present invention.

As summarized above, the present invention is a method and apparatus for automatic sampling of fibers as they fall within a fiber chute. The invention requires both static air pressurization of the sampler housing and a rod-like sample probe of specific design.

The sampler housing may be constructed of any material which is substantially air impermeable and sufficiently strong to support itself, the sampler interior components, the air blower and the associated fiber discharge chute. Suitable materials include aluminum and steel. Steel is preferred due to its strength. Stainless steel is most preferred due to its resistance to corrosion by fiber finish compositions which have been applied to the staple fiber earlier in the manufacturing process.

The means for attachment of the sampler housing to a sample port on the fiber chute to be sampled may be constructed of the same material as the sampler housing. The attachment means may comprise a series of bolts and nuts around the periphery of the sample port, which may be circular, rectangular, or square. The attachment means should attach the sampler housing securely to the sample port, and is preferably air tight.

It should be noted that the present invention does not require sealing means, such as a door, to close off the sample port of the fiber chute when the falling fibers are not being sampled.

A small constant speed electric fan or blower may conveniently be used as the means for maintaining the air pressure within the sampler housing substantially equivalent to the air pressure within the fiber chute. Air flow through the fan may be controlled by a "damper". Air pressure equalization can be checked by suspending a short length of string from the sample port. If the air pressure inside the fiber chute is greater than the sampler housing air pressure, the string will be blown towards the sampler. If the air flow through the fan is then increased beyond what is required to equalize the air pressure within the fiber chute and the sampler interior, the string will be blown towards the fiber chute. In place of an electric fan, a pressurized air flow from any convenient source may be employed. It will be understood that the sampler air pressure should be maintained equivalent to the fiber chute air pressure whenever fiber is falling within the fiber chute, regardless of whether the sampler is in use.

The sample discharge chute is attached to the bottom of the sampler housing, and may be fabricated from the same materials as the sampler housing. Preferably, at least a portion of the sample discharge chute may be formed as an integral part of the sampler housing. Smooth transition and snag-free interior surfaces of both the sampler housing and the sample discharge chute are important to effective sampling.

The rod-like sample probe must have a smooth, convex fiber-sampling section at one rounded end and, opposite thereto, a mounting means engagement end. The smooth, convex fiber-sampling section extends from the rounded end towards the opposite end of the rod-like sample probe for at least two inches, and preferably at least six inches. The fiber-sampling section must have at least one protrusion mounted at or near the rounded end of the rod-like sample probe.

The fiber-sampling end of the rod-like sample probe must be rounded (i.e. snag-free) so that fibers which are falling in the fiber chute to be sampled do not catch on any sharp edges or surfaces. Staple polyester fiber which has been crimped has a tendency to intertwine with similar fibers, thereby forming string-like "rat tails". Such fiber also has a tendency to catch on sharp corners, scratched surfaces or protrusions.

The mounting means engagement end of the rod-like sample probe should be designed to securely attach the rod-like sample probe to the reciprocating insertion/retraction and rotation means discussed below. Such mounting means may be a ball detent, a key and chuck arrangement, a threaded hole adapted to receive a mounting bolt, or any other equivalent attachment device.

The smooth, fiber-sampling section of the rod-like sample probe must be smooth and convex with respect to the falling staple fibers. By "convex" it is meant a rounded, as opposed to flat or concave, surface upon which the falling staple fibers can drape themselves. The "convex" fiber-sampling section surface requirement may be satisfied by a cylindrical, semi-cylindrical, or ellipsoidal rod-like sample probe.

It should be emphasized that the contour of the smooth, fiber-sampling section of the rod-like sample probe is critical to successful sampling of staple fibers. By "successful sampling" it is meant reproducible sampling which does not significantly affect or alter the properties of the sampled staple fibers. The fiber-sampling section of the rod-like sample probe must present a convex surface to the falling staple fibers. Other sampling surfaces have been evaluated and found unsuccessful. A flat, wide sampling surface with eight large protrusions sampled excessive amounts of fiber, and was not reproducible. A cylindrical sampling probe which was curved at the fiber-sampling end into an upwardly pointing hook was unsatisfactory because staple fibers would slide toward the horizontal section, bunch, tangle, and not fall off upon retraction and rotation (inversion) of the hook. A horizontally surfaced sampling probe without any protrusions was also unsuccessful, as were scooped (concave) sampling probes. It became apparent that the contour or geometry of the sampling probe was important to the utility of a staple fiber sampling apparatus.

A smooth surface may be achieved by deburring and polishing the fiber-sampling section, including the rounded end and the protrusion. A smooth, snag-free fiber-sampling section surface is critical to effective statistically representative sampling. Such a smooth surface ensures adequate release of sampled fiber from the rod-like sample probe after it has rotated about its major axis into its fiber discharge position by preventing sample "hangs" and the initiation of "rat-tails". Incomplete release or discharge of the sampled staple fiber reduces sample mass reproducibility and permits potential contamination of subsequent fiber samples.

An empirical method for determining whether an apparently smooth surface is sufficiently smooth for use in the present invention involves rubbing a ladies' stocking filled with staple fiber over the candidate surface. If the stocking slides smoothly over the surface without catching on any burrs, scratches, or protrusions, the candidate surface is sufficiently smooth for use as the fiber-sampling section surface in the present invention.

The rod-like sample probe may be fabricated of any sufficiently rigid, sufficiently smooth material. Stainless steel tubing having an outside diameter of 1.5 inches is preferred, although small or larger diameter may be more appropriate for certain length fibers. The length of the rod-like sample probe should be sufficiently long to extend at least partway into the fiber chute to be sampled when the reciprocating insertion/retraction means, discussed below, have extended the rod-like sample probe to the fully inserted position. The length of the rod-like sample probe should not be so great so that any portion of the probe remains in the fiber chute when the reciprocating insertion/retraction means have fully retracted the rod-like sample probe. A representative length is fifteen inches.

The smooth, convex fiber-sampling section of the rod-like sample probe member must have at least one protrusion at or near the rounded end of the rod-like sample probe. By "protrusion" it is meant a vertical, upwardly pointing, preferably circular, post having an outside diameter of about ½ inch, although smaller or larger diameter may be more appropriate for certain fibers. The protrusion should have a smooth surface, be rounded at the top, and be securely and smoothly mounted to the smooth, convex fiber-sampling section. The protrusion may preferably be machined from ½ inch diameter stainless steel rod.

The "first, fiber-sampling position" of the rod-like sample probe is defined as that position where the protrusion points substantially vertically upward, and contrary to the direction of travel of the staple stream to be sampled. The "second, fiber-discharge position" of the rod-like sample probe is defined as that position where the protrusion has been rotated more than 90 degrees and is pointing downward. Preferably, the "second, fiber-discharge position" of the rod-like sample probe is at least 150 degrees, most preferably 180 degrees, from said "first, fiber-sampling position" of the rod-like sample probe.

The function of the protrusion(s) is three-fold; first, it prevents sampled staple fibers, which are draped over the smooth, convex surface of the fiber-sampling section of the rod-like sample probe from sliding off the rounded end of the rod-like sample probe as it is retracted from the fiber chute. Second, the protrusion serves to ensure that the sampled staple fibers will "follow" the rod-like sample probe as it rotates about its major axis to the second, fiber-discharge position. The protrusion serves to carry or urge the mass of sampled staple fibers with it as it rotates to a downwardly pointing position, thereby reducing the possibility that the sampled staple fibers will remain on the top of the rod-like sample probe which is rotating underneath the staple fiber mass. Finally, the number and height of protrusion(s) determine, in part, the quantity of fiber sampled in each sampling operation.

The inventor has found that a rod-like sample probe possessing a rounded end and a smooth, convex fiber-sampling section but having no protrusion is not effective as a staple fiber sample probe. In short, the smooth, convex fiber-sampling section must have at least one protrusion mounted thereon in order to successfully sample staple fiber falling within a fiber chute under the influence of gravity. Increasing the number of protrusions and the height of the protrusion will generally increase the amount of staple fiber which is sampled per sampling cycle, assuming other conditions, such as sampling time, are kept constant. If these conditions are kept constant, it is possible to determine the optimum number and height of protrusions for various staple fiber lengths. The shorter and generally finer staple fiber products (i.e. nominal lengths of less than 2.5 inches) require a greater amount of sample per sampling cycle to achieve a given level of statistical certainty than relatively longer and coarser staple fiber products (i.e. nominal lengths of greater than 2.5 inches). The preferred sample probes for conventional, crimped polyester staple fiber products, ranging in length from 1.5 to 7.5 inches in nominal fiber length, will employ one or two protrusions mounted on the smooth, convex fiber-sampling section ranging from ⅜ to ½ inches in "effective height" (i.e. that distance from a plane tangent to the rod-like sample probe to the spherically rounded end of the protrusion). The surface geometry permutations which can be designed for a smooth, convex fiber-sampling surface using one or two protrusions, of the same or different effective height, and mounted at or near the rounded end of the rod-like sample probe, can provide a statistically representative composite staple fiber sample using a sampling frequency of from 30 to 50 sampling cycles per bale of fiber.

The means for retractably inserting the rod-like sample probe into the fiber chute must provide for reciprocal movement of the rod-like sample probe along its major axis through the sampling port into the fiber chute and back within the sampler housing. Such insertion/retraction means are well known in the art and may preferably comprise at least one dual action rodless air cylinder, aligned parallel to the major axis of the rod-like sample probe and attached thereto by means of a carriage through which the rod-like sample probe is journalled and supported by bearings to permit rotation of the rod-like sample probe about its major axis. A pair of such dual action, rodless air cylinders, mounted in opposed, parallel relationship, is even more preferred since the second air cylinder provides an additional attachment point to the carriage, thereby reducing undesirable translational motion by the rod-like sample probe around its major axis. Such undesirable translational motion by the sample probe could exert a significant moment, or torque, upon a single rodless air cylinder, thereby causing excessive wear.

Pneumatic and mechanical means for rotating the rod-like sample probe about its major axis are also well known. U.S. Pat. No. 3,949,614 discloses a mechanical groove and finger member design which rotates an elongated sampling probe about its major axis as the probe is inserted and retracted from a sampling zone. The preferred embodiment of the present invention employs a ball bearing fixed within the carriage supporting the rod-like sample probe in cooperating relationship with a semi-helical groove on the surface of an auxilliary shaft axially rotably mounted within the carriage and axially attached to and aligned with the rod-like sample probe. The auxilliary shaft with the semi-helical groove acts as a three dimensional cam while the fixed ball bearing functions as a cam follower and is necessarily free to roll about its centroid. The groove is sufficiently long to permit more than 90 degree rotation of the auxilliary shaft and, therefore, the rod-like sample probe from a first, fiber-sampling position to a second, fiber-discharging position. The helical groove is preferably long enough to permit 180 degree rotation of the rod-like sample probe from its first, fiber-sampling position to its second, fiber-discharging position. In the preferred embodiment, the ball bearing also serves to fix the rod-like sample probe to the carriage which inserts and retracts the rod-like sample probe into the fiber chute under the action of the rodless air cylinders.

The rod-like sample probe may be maintained in its first, fiber sampling position by means of a spring which is held in compression against the rear of the sample probe carriage by a bolt and plug or other mounting means which engages the mounting means engagement end of the rod-like sample probe.

While the fiber sampler of the present invention can be either manually or automatically operated, automatic operation is preferred, since this eliminates any sampling bias due to worker fatigue or inattention. The actual control circuits are conventional and need not be described in detail. Operation based upon mass flow of the staple fibers is preferred and more statistically accurate than time dependent sampling if regular rather than random sampling is desired. U.S. Pat. Nos. 3,841,159; 3,315,530,530; and 4,024,765 all cite time dependent sampling of flowing materials. Mass flow sampling of the fibers may conveniently be effected by making sampling frequency dependent upon the speed of the fiber cutting apparatus.

DESCRIPTION OF A PREFERRED EMBODIMENT

The present invention may be further illustrated by description of a preferred embodiment. Referring to FIG. 1, staple fibers 1 are falling within the confines of fiber chute 5 towards baler 10. Fiber sampler housing 15 is attached to sample port 20 by attachment means (not shown). The air pressure within the sampler housing is maintained substantially equivalent to the air pressure within the fiber chute by air blower 25. Rod-like sample probe 30 is supported within the sampler housing by carriage 35, which is attached to parallel, opposed rodless air cylinders 40. A fiber discharge chute 45 is attached to the bottom of sampler housing 15. Staple fiber fly guard plate 37 is attached to carriage 35 and serves to minimize the possibility of staple fibers contaminating the recesses of the sampler rather than dropping into fiber discharge chute 45.

Figure 2:
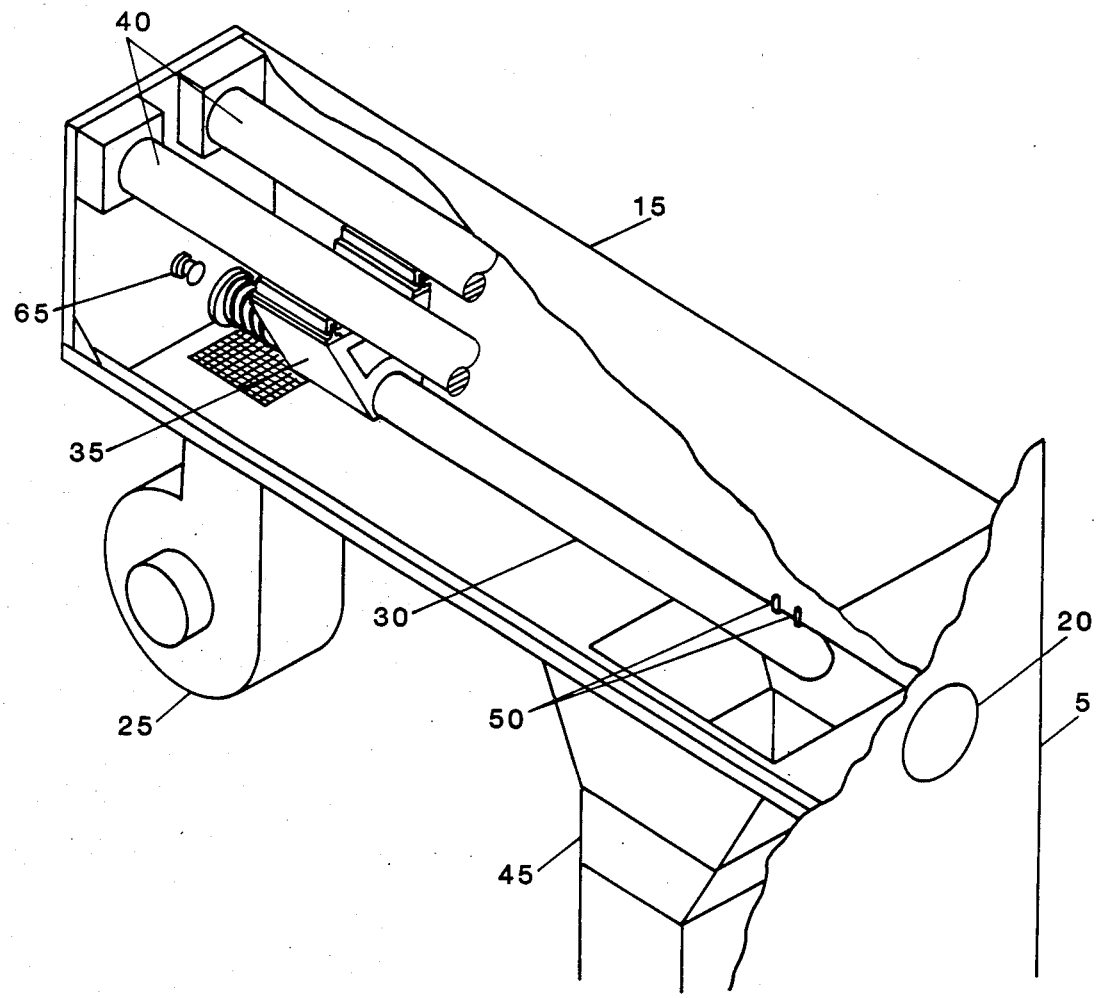
FIG. 2 is an isometric view from the left side of the fiber sampler of the present invention in its non-sampling position.

The practice and advantages of the present invention may be further illustrated by referring to FIGS. 2 through 6, which depict the above-described sampler in sequential stages of operation. Staple fiber fly guard plate 37 is not shown in FIGS. 2 through 6 in order to more clearly illustrate the sequential operation of the invention. Referring to FIG. 2, the sampler is in a non-sampling position, with rod-like sample probe 30 completely within sampler housing 15. Rod-like sample probe 30 is in a "fiber-sampling position", with protrusions 50 in a vertical, upwardly pointing position.

Figure 3:
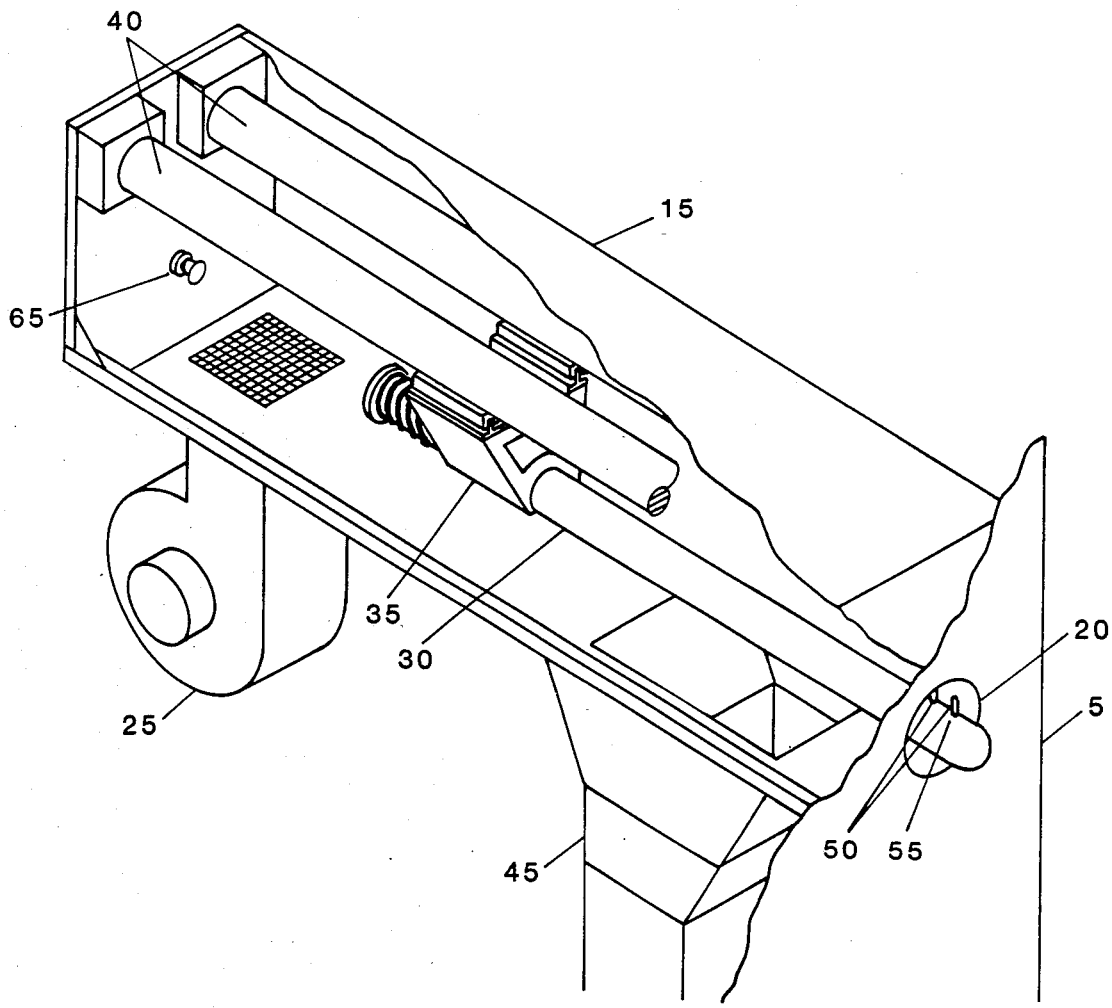
FIG. 3 is an isometric view from the left side of the fiber sampler of the present invention illustrating the initiation of the sampling procedure.

FIG. 3 depicts the initiation of the sampling operation. Rodless air cylinders 40, acting through carriage 35, have urged rod-like sample probe 30 partially through sample port 20 into fiber chute 5.

Figure 4:
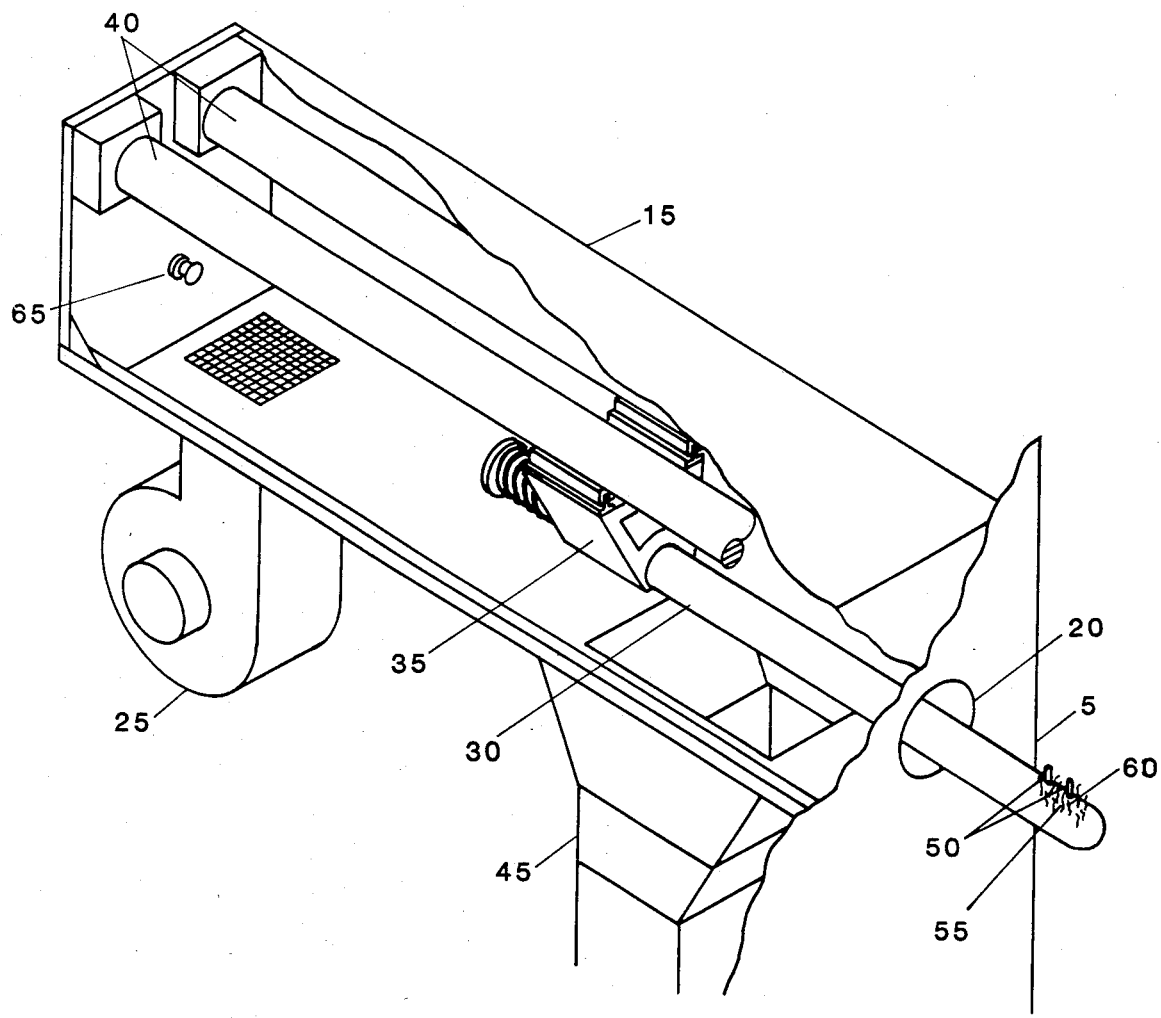
FIG. 4 is an isometric view from the left side of the fiber sampler of the present invention illustrating the rod-like sample probe in its sampling position.

FIG. 4 depicts rod-like sample probe 30 at its farthest extension into fiber chute 5. A portion of staple fibers 1, falling within fiber chute 5 under the influence of gravity, fall upon and drape themselves over protrusions 50 and the smooth, convex surface of fiber-sampling section 55 of rod-like sample probe 30.

Figure 5:
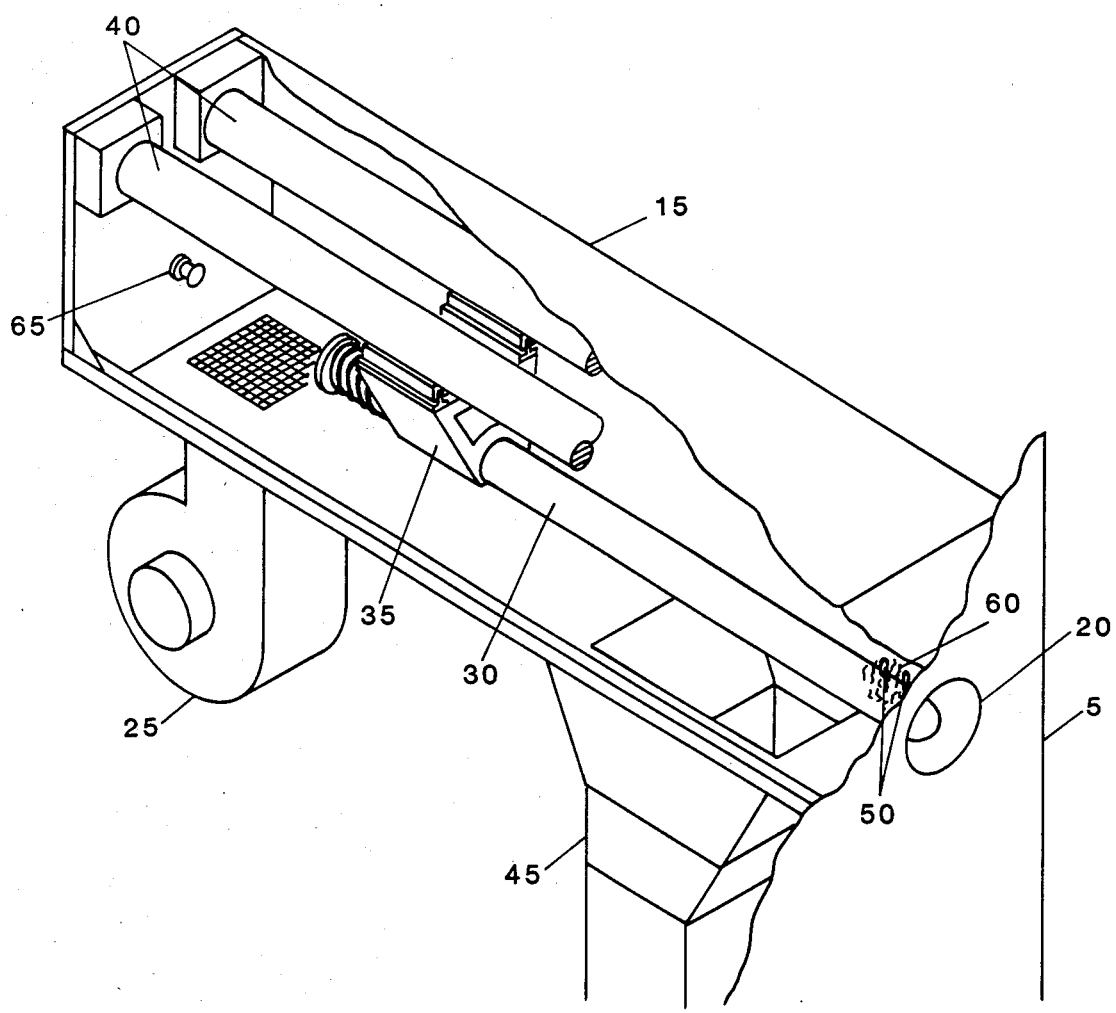
FIG. 5 is an isometric view from the left side of the fiber sampler of the present invention illustrating the withdrawal of the rod-like sample probe from the fiber chute.

FIG. 5 depicts the withdrawal of rod-like sample probe 30 from the fiber chute 5 through sample port 20, by the carriage 35 under the urging of rodless air cylinders 40. Sample staple fibers 60 remain on the smooth, convex surface of fiber-sampling section 55 due to protrusions 50.

Figure 6:
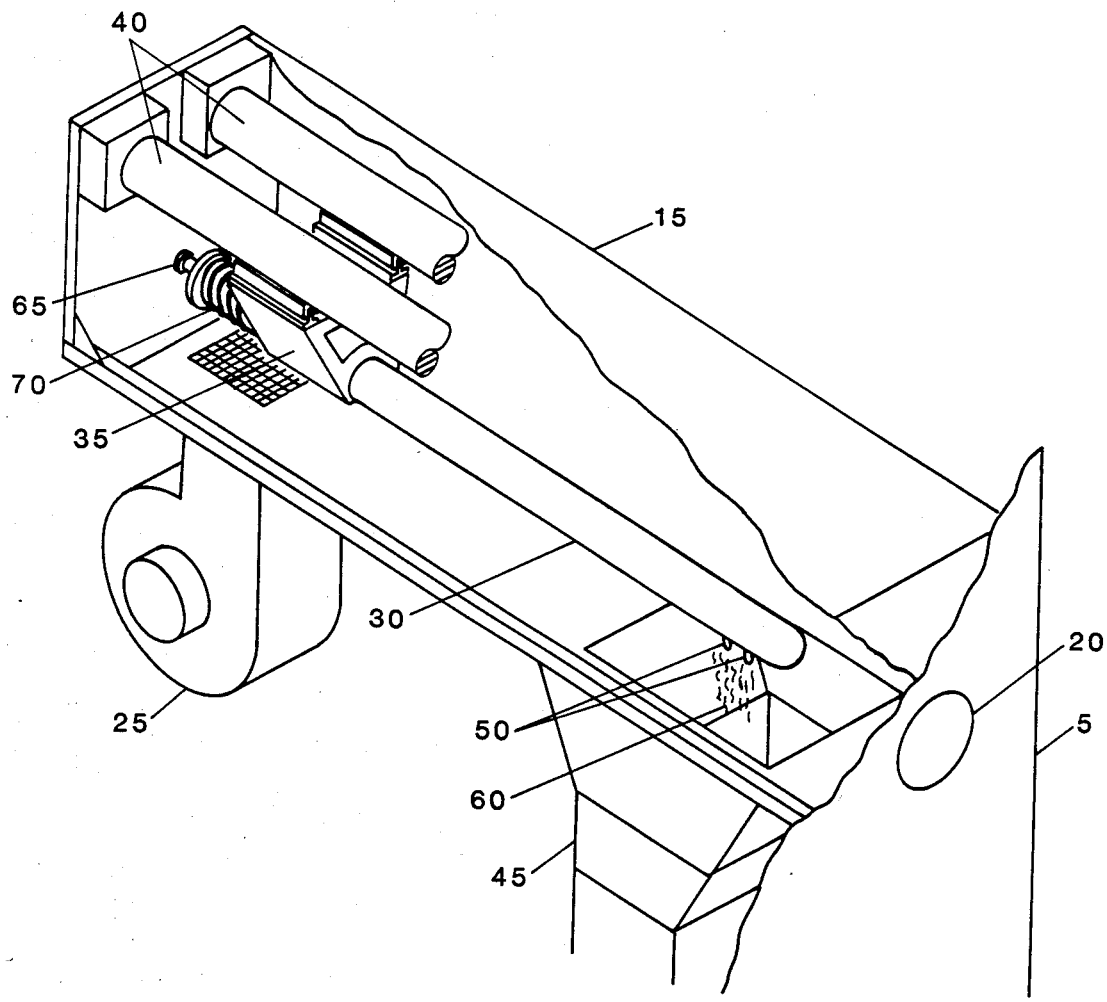
FIG. 6 is an isometric view from the left side of the fiber sampler of the present invention illustrating the rotation of the rod-like sample probe into its second, fiber-discharging position.

FIG. 6 depicts the discharge of sample staple fibers 60 from smooth, convex fiber-sampling section 55 due to the rotation of rod-like sample probe 30 from a first, fiber-sampling position to a second, fiber-discharging position. This rotation of rod-like sample probe 30 about its major axis is due to the urging of rod-like sample probe 30 by the action of rodless air cylinders 40 against bumper 65, thereby forcing rod-like sample probe 30 to rotate through a semi-helical movement. Sample staple fibers 60 will then fall from the smooth, convex surface of the fiber-sampling section 55 into sample discharge chute 45.

As soon as rodless air cylinders 40 cease urging rod-like sample probe 30 against bumper 65, spring 70 will return same to its first, fiber-sampling position. This takes place at the beginning of the next, discrete sampling cycle.

Figure 7:
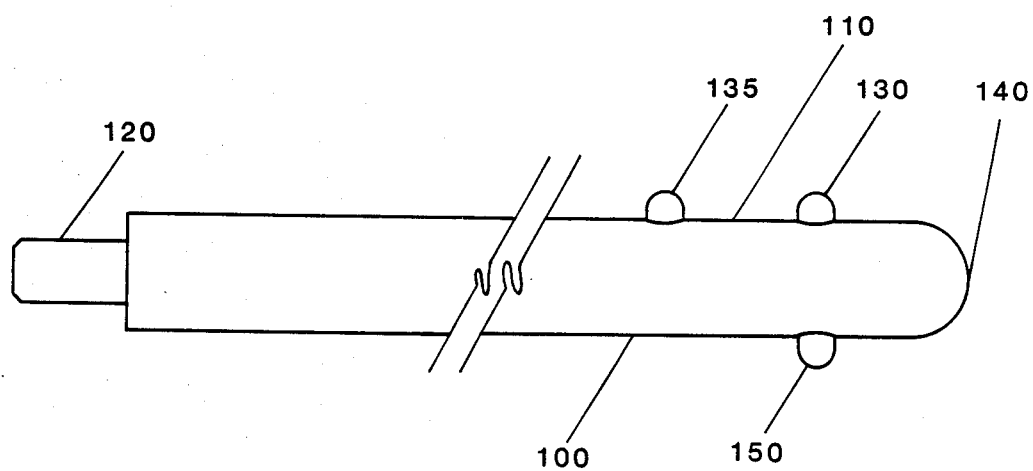
FIG. 7 is a side view of a preferred embodiment of the rod-like sample probe of the present invention.
Figure 8:
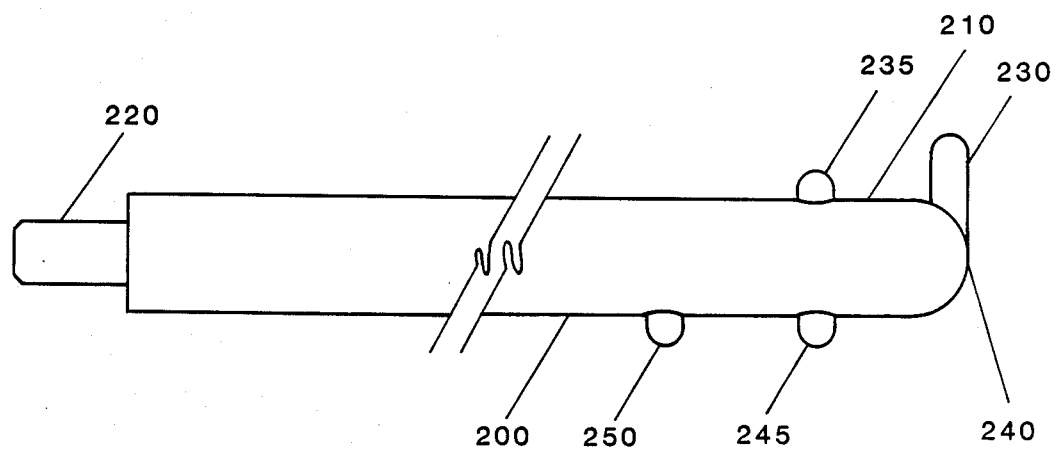
FIG. 8 is a side view of a second preferred embodiment of the rod-like sample probe of the present invention.

FIGS. 7 and 8 depict preferred embodiments of the rod-like sample probe in their first, fiber-sampling positions. Referring to FIG. 7, rod-like sample probe 100 has a smooth, convex fiber-sampling section 110 at one rounded end 140 and, opposite thereto, a mounting means engagement end 120. Protrusion 130 is approximately two inches from rounded end 140, with protrusion 135 approximately four inches from rounded end 140. The total length of rod-like sample probe 100 is typically between 10 and 15 inches. The particular rod-like sample probe 100 illustrated in FIG. 7 is "reversible". By simply detaching rod-like sample probe 100 from the means for attachment to the carriage, rotating the rod-like sample probe 180 degrees so that protrusion 150 is pointing upward, and reattaching rod-like sample probe 100 to the means for attachment to the carriage, a different convex sampling surface geometry can be presented to the falling staple fibers FIG. 8 additionally illustrates a two-protrusion sample probe wherein the "effective heights" of the protrusions are different. Protrusion 230, for example, may have an effective height of $\frac{1}{2}$ inch, while protrusion 235 may have an effective height of $\frac{3}{8}$ inch.

FIG. 8 is similar to FIG. 7 in that it depicts a "reversible" rod-like sample probe 200 having a smooth, convex fiber-sampling section 210 at one rounded end and, opposite thereto, a mounting means engagement end 220. Protrusion 230 is depicted at the end 240 of rod-like sample probe 200, with protrusion 235 being located approximately 2 inches from rounded end 240. The total length of rod-like sample probe 200 is typically between 10 and 15 inches. A different sampling surface geometry can be presented to the falling staple fibers by simply disengaging rod-like sample probe 200 from the means for attachment of the sample probe to the carriage, rotating the rod-like sample probe 180 degrees so that protrusions 245 and 250 are pointing upwardly, and reattaching rod-like sample probe 200 to the means for attachment of the sample probe to the carriage.

The preferred "reversible" rod-like sampling probes depicted in FIGS. 7 and 8—each having two separate smooth, convex fiber-sampling sections 180 degrees opposed from the other—permit rapid and convenient fiber sampling modifications in response to intentional staple fiber product changes and changed statistical sampling requirements.

Obviously, the specific embodiments of the present invention are merely specific, non-limiting illustrations of the broad inventive concept of employing a smooth, convex surface, having at least one protrusion thereupon, in combination with equivalent air pressurization, to sample falling staple fibers. One of ordinary skill in the art, having read this disclosure, will be able to construct variations of the specific embodiments disclosed herein and remain well within the scope and spirit of the present invention.

I claim:

1. An apparatus for sampling staple fibers which are falling within a fiber chute comprising
   (i) a sampler housing;
   (ii) means for attachment of said sampler housing to a sample port on said fiber chute;
   (iii) means for maintaining the air pressure within said sampler housing substantially equivalent to the air pressure within said fiber chute;
   (iv) a sample discharge chute attached to said sampler housing;
   (v) a rod-like sample probe mounted within said sampler housing having a smooth, convex fiber-sampling section at one rounded end and, opposite thereto, a mounting means engagement end, said fiber-sampling section having at least one protrusion mounted at or near said rounded end;
   (vi) means for retractably inserting said rod-like sample probe from within said sampler housing into said fiber chute perpendicularly to the direction of fiber travel;
   (vii) means for rotating said rod-like sample probe more than 90 degrees about its major axis from a first, fiber-sampling position to a second, fiber-discharging position;
   (viii) means for controlling the movements of said rod-like sample probe by the retractable insertion means and the rotation means.

2. The apparatus of claim 1 further comprising means for minimizing staple fiber contamination of the apparatus.

3. The apparatus of claim 2 wherein the fiber-sampling section of said rod-like sample probe is a full cylinder.

4. The apparatus of claim 2 wherein the fiber-sampling section of said rod-like sample probe is an ellipsoid.

5. The apparatus of claim 2 wherein said rod-like sample probe has at least two protrusions on said fiber-sampling section.

6. The apparatus of claim 5 wherein said protrusions are the same effective height and diameter.

7. The apparatus of claim 5 wherein said protrusions have different effective heights.

8. The apparatus of claim 2 wherein said means for minimizing staple fiber contamination of the apparatus comprise a planar member mounted vertically on a means for mounting said rod-like sample probe to said sampler housing.

9. The apparatus of claim 2 wherein said rod-like sample probe rotates more than 120 degrees about its major axis from said first, fiber-sampling position to said second, fiber-discharging position.

10. The apparatus of claim 9 wherein said rod-like sample probe rotates more than 150 degrees about its major axis from said first, fiber-sampling position to said second, fiber-discharging position.

11. The apparatus of claim 10 wherein said rod-like sample probe rotates 180 degrees about its major axis from said first, fiber-sampling position to said second, fiber-discharging position.

12. A process for sampling staple fibers which are falling within a fiber chute comprising:
   (i) maintaining the air pressure within a sampler housing, which is attached to a sample port on said fiber chute, substantially equivalent to the air pressure within said fiber chute;
   (ii) inserting a rod-like sample probe mounted within said sampler housing through said sample port into said fiber chute;
   (iii) collecting a sample of fibers falling within said fiber chute on said rod-like sample probe;
   (iv) retracting said rod-like sample probe, bearing said fiber sample, through said sample port and into said sampler housing;
   (v) rotating said rod-like sample probe more than 90 degrees about its major axis, thereby discharging said fiber sample into a sample discharge chute mounted onto the bottom of said sampler housing; with the proviso that said rod-like sample probe has a smooth, convex fiber-sampling section at one rounded end and, opposite thereto, a mounting means engagement end, said fiber-sampling section having at least one protrusion mounted at or near said rounded end.

13. The process of claim 12 wherein said rod-like sample probe is rotated at least 120 degrees about its major axis to discharge said fiber sample.

14. The process of claim 13 wherein said rod-like sample probe is rotated at least 150 degrees about its major axis to discharge said fiber sample.

15. The process of claim 14 wherein said rod-like sample probe is rotated 180 degrees about its major axis to discharge said fiber sample.

16. The process of claim 12 wherein said rod-like sample probe is a full cylinder.

17. The process of claim 12 wherein said rod-like sample probe is an ellipsoid.

18. The process of claim 12 wherein said sampler further comprises means for minimizing staple fiber contamination of the sampler.

19. The process of claim 18 wherein said means for minimizing staple fiber contamination of the sampler comprise a planar member mounted vertically on a means for mounting said rod-like sample probe to said sampler housing.

* * * * *